United States Patent
Kream (10) Patent No.: US 6,881,829 B2
(45) Date of Patent: Apr. 19, 2005

(54) CHIMERIC HYBRID ANALGESICS

(75) Inventor: Richard M. Kream, Huntington, NY (US)

(73) Assignee: Chimeracom, L.L.C., New York, NY (US)

( * ) Notice: Subject to any disclaimer, the term of this patent is extended or adjusted under 35 U.S.C. 154(b) by 68 days.

(21) Appl. No.: 10/134,187

(22) Filed: Apr. 26, 2002

(65) Prior Publication Data

US 2003/0202981 A1 Oct. 30, 2003

(51) Int. Cl.$^7$ .......................... C07K 1/00; C07K 14/00; C07K 17/00; A61K 38/00
(52) U.S. Cl. .................... 530/402; 530/350; 530/300
(58) Field of Search ............................. 530/300, 350, 530/402

(56) References Cited

U.S. PATENT DOCUMENTS

| | | |
|---|---|---|
| 5,891,842 A | 4/1999 | Kream |
| 6,063,758 A | 5/2000 | Lappi et al. |
| 6,310,072 B1 | 10/2001 | Smith et al. |

FOREIGN PATENT DOCUMENTS

| | | |
|---|---|---|
| WO | WO 01/30371 A | 5/2001 |

OTHER PUBLICATIONS

Lipkowski, et al, Neuropeptides: Peptide and Nonpeptide Analogs, Peptides: Synthesis, Structures and Applications. 1995, pp 287–320. Academic Press.
Reuler, et al., *The Chronic Pain Syndrone: Misconceptions & Management*, Ann Intern Med. 93:588–596 (1980).
Sriwatankul, et al, *Analysis of Narcotic Analgesic usage in the Treatment of Postopertive Pain*, JAMA 250:926–929 (1983).
Schechter, *Pain & Pain Control in Children*, Current Problems in Pediatrics 15 (1985).
Goodman & Gilman, *The Pharmacological Basis of Therapeutics* 511 ($7^{th}$ ed. 1985).
Foran, et al, *A Substance P–opioid chimeric peptide as a unique nontolerance–forming analgesic*, 97 PNAS 13:7621–26 (2000).
Egelton, et al, *Transport of Opioid Peptides into the Central Nervous System*, J Pharm Sci 1998, 87(11):1433–39.
Borchard, *Optimizing oral absorption of peptides using prodrug strategies*, J Control Release 1999; 62(1–2):231–38.
Stain–Texier, *Elevated concentrations of morphine 6–beta–D–glucuronide in brain extracellular fluid despite low blood–brain barrier permeability*, Br J Pharmacol 1999; 128(4):917–24.
Merrifield, *Solid Phase Synthesis*, Science 232: 241–47 (1986).
Barany, et al, *Solid–phase peptide synthesis; a silver anniversary report*,Int'l J Peptide Protein Res 30:705–39 (1987).
Kent, *Chemical Synthesis of Peptides and Proteins*, Ann Rev Biochem 57:857–989 (1988).
Kaiser, et al, *Peptide & Protein Synthesis by Segment Synthesis–Condensation*, Science 243:187–98 (1989).

(Continued)

Primary Examiner—Brenda Brumback
Assistant Examiner—Robert S. Landsman (57) ABSTRACT

The present invention provides composition of matter for and methods of treating pain and drug abuse using novel chimeric hybrid molecules containing an opioid moiety of chemically modified morphine (3) that binds to and activates the human mu ($\mu$) opioid receptor, with the opioid moiety linked through a novel linker-hinge (4) to a substance P peptide fragment moiety (5) that binds to and activates the human substance P receptor. The hybrid alkaloid/peptide chimeric molecules produce clinically efficacious opioid analgesia with little or no development of opioid tolerance or formation of opioid dependence. The hybrid alkaloid/peptide analgesics may be administered intrathecally, systemically or orally.

36 Claims, 1 Drawing Sheet

OTHER PUBLICATIONS

Kream, *Substance P markedly potentiates the antinocicpetive effects of morphine sulphate administered at the spinal level*, 90 PNAS 5564–68 (1993).

Masczynska, et al, *Alternative forms of interaction of substance P and opioids innocicpetive transmission*, LTRS Peptide Sci 298, 5:395–98 (1998).

Masczynska, et al, *Dual Functional Interactions of Substance P Opioids in Nociceptive Transmission*, Analgesia 3:259–68 (1998).

Watson, et al, *Tissue Selectivity of Substance P Alkyl Esters Suggesting Multiple Receptors*, Euro J Pharmacol 87:77–84 (1983).

Sizheng, et al, *Opioid and neurokinin activities of substance P fragments and their analogs*, Euro J Pharamcol 193:209–15 (1991).

Lipkowski, et al, *An Approach to the Self Regulatory Mechanism of Substance P Actions*, 33 Life Sciences 141–44 (1983).

Foran, et al, *Inhibition of Morphine tolerance Development by a Substance P–Opioid Peptide Chimera*, J Pharamcol & Ex Thera 295:3:1142–48 (2000).

Lipkowski, et al, *Opioid Peptide Analogues: Reconsideration as a Potentially New Generation of Analgesics*, Polish J Chem, 68:907 12 (1994).

Misterek, et al, *Spinal Co–Administration of Peptide Substnace P Antagonist Increases Antinociceptive Effect of the Opioid Peptide Biphalin*, 54 Life Sciences, 14:939–44 (1994).

Foran, et al, *Chimeric Peptide for the Treatment of Acute & Chronic Pain* Anesthesiology 91:3A:A944 (1999).

Langel, et al, *Design of chimeric peptide ligands to galanin receptors and substance P receptors*, Intl J Peptide & Protein Res 39:6:516–522 (1992).

Cavagnero, et al, *Delta opioid Receptor Selectivity Ligands*, 49 Life Sciences 495–503 (1991).

Carr, et al, *Mechanisms of Opioid Analgetic Actions*, 1 Principles & Practice of Anesthesiology, Ch 32 (1993).

CHIMERIC HYBRID ANALGESICS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISK APPENDIX

A written Sequence Listing and a computer readable form of the sequence listing, consisting of one file named ChimericHybridAnalgesics.ST25.txt on one disk, are attached as Appendices.

BACKGROUND OF THE INVENTION

1. Field of the Invention

The present invention lies firmly within the fields of drug, bio-effective and body treating compositions, more specifically drugs and methods for acute and chronic pain relief and acute and chronic intervention for drug abuse.

2. Description of the Prior Art

The present invention relates to novel hybrid alkaloid/peptide chimeric molecules for the treatment of pain. The relief of suffering due to pain is an important objective of clinical practice and for restoring quality to life and the ability to function normally to pain sufferers.

Pain represents an integrated, complex, perception of noxious stimuli originating from somatic elements such as arms and legs and/or from visceral organs such as heart and liver. Mechanistically, acute pain signaling involves noxious stimulation of free nerve endings innervating somatic elements and/or visceral organs leading to the activation of different types of slowly-conducting afferent fibers of the A delta and C classes, terminating in the dorsal sensory spinal cord. A significantly more complex etiology underlies the initiation and persistence of chronic pain syndromes. This involves initial damage to peripheral nerves innervating somatic and visceral fields, persistent immunological challenge by cytokines and inflammatory mediators, reorganization of spinal cord and brainstem relay systems, and higher cortical adaptation.

From an established pharmacological perspective, opioids remain the key agents of choice for treatment of a wide variety of acute and chronic pain states. The prototype opioid analgesic or painkiller is morphine. Morphine and morphine-related opioids produce their painkilling effects by profound pharmacological inhibition of neurons of the peripheral/sensory nervous system (PNS) and the central nervous system (CNS). The biochemical and cellular effects of morphine, including profound analgesia, are transduced through a membrane-associated G-protein designated the mu ($\mu$) opioid receptor (MOR), found in high concentrations within the PNS and CNS.

Unfortunately, the high degree of pain relief afforded by morphine and similar opioid compounds is associated with many undesirable side effects, all mediated through activation of the MOR. They include drowsiness, nausea, emesis (vomiting), changes in mood (dysphoria), respiratory depression, decreased gastrointestinal motility (constipation), pruritis (itching), alterations in endocrine and autonomic function, and physical and psychological dependence leading to addiction.

In addition to the adverse physiological sequelae listed above, a major associated risk is that repeated daily administrations of morphine or morphine-like opioids will eventually induce significant tolerance to the therapeutic effects of the drug as well as initiating some degree of physical dependence. Here opioid tolerance is operationally defined as an escalating dosage regimen required to achieve the same magnitude of pain relief over a defined time course.

The administration of escalating dosage so as to achieve the same magnitude of pain relief can increase the likelihood and the severity of undesirable side effects such as drowsiness, nausea, emesis (vomiting), changes in mood (dysphoria), respiratory depression, decreased gastrointestinal motility (constipation), pruritis (itching), alterations in endocrine and autonomic function.

The degree of tolerance and physical dependence will vary with the particular opioid employed, the correlation with MOR-selective opioids such as morphine being high, the frequency of administration, and the quantity of opioid administered.

In a wide variety of clinical indications requiring prolonged use of opioids, tolerance induction and addiction are closely linked, with the development of physical and psychological dependence always a major concern. Addiction with physical dependence can be difficult to treat due to the effects of withdrawal associated with dependence.

From an established clinical perspective, when morphine and/or similar opioid analgesics are administered, the treating health care provider must recognize that only symptomatic treatment of pain is being provided. The health care provider must therefore constantly weigh the benefits of this immediate (day by day) relief against its costs and risks to the patient. Accordingly, a decision to relieve the chronic pain in particular clinical situations via administration of current opioid analgesics may be short sighted and an actual disservice to the patient.

Morphine and related MOR-selective opioids also relieve suffering by ameliorating the emotional or affective component of the painful experience. Consequently, if little or no external emotional support is provided, for example by biofeedback procedures or cognitive behavioral therapy, some patients may require considerably more than the average dose of an opioid to experience any relief from pain; similarly, others may require more frequent administration. These are major factors supporting the use of patient-controlled analgesia (PCA) for acute post-operative pain control, where the affective aspects of painful experience are successfully addressed. In effect, many health care providers frequently tend to prescribe therapeutic dosages of opioids that are either too low and/or administered at infrequent time intervals out of an exaggerated concern for minimizing addiction potential. The resultant therapeutic regimen fails to provide adequate analgesia over time.

In light of the caveats listed above, many health care providers are constantly encouraged to employ measures other than opioid drugs to relieve chronic or acute pain, even when such alternative methods show limited efficacy in the absence of opioid therapy. These typically include the use of local nerve block, combinations of antidepressant and anticonvulsant CNS drugs, electrical stimulation, acupuncture, hypnosis, or behavioral modification (Reuler et al., Ann. Intern. Med. 93:588–596 (1980)). Additionally, many practitioners respond to their patients' continued complaints of inadequate pain relief with even more exaggerated concerns about dependency. This is done despite the high probability that the request for more opioid is only the expected consequence of the inadequate dosage originally prescribed. (Sriwatanakul et al., J.A.M.A. 250:926–929 (1983))

It has also been documented that children are probably more apt to receive inadequate dosages for pain than are adults based on the same type of reasoning concerning tolerance and dependence Schechter. (N. L., Curr. Probl. Pediatr. 15 (1985))

Finally, it is useful to remember that the typical initial dose of morphine (10 mg/70 kg body weight) relieves post-operative pain satisfactorily in only about two-thirds of patients. (See page 511, Gilman et al., The Pharmacological Basis of Therapeutics)

Morphine/opioid-induced physiological and psychological side effects pose major obstacles to their unfettered, widespread usage as the mainspring therapeutic regimen for pain relief across clinical populations in the United State and abroad. Intrinsic issues of opioid safety and efficacy were addressed by a prior invention (U.S. Pat. No. 5,891,842), where I established a therapeutic procedure or treatment regimen for inducing or eliciting a markedly enhanced opioid-dependent analgesic response within a living subject. That treatment methodology employs the concurrent administration of two recognized, self-contradicting and physiologically antagonistic compounds, the opioid analgesic morphine sulfate and the tachykinin peptide substance P(SP), at individual concentrations that had been empirically shown to have either marginal or completely ineffectual pharmacological properties in vivo. Because noxiously challenged or damaged sensory nerves release a variety of excitatory chemical mediators, including SP, the tachykinin SP had been previously designated as a nociceptive or pain-producing peptide transmitter at the spinal level. Nevertheless, my research demonstrates that at concentrated low nanogram concentrations SP appears to be a potent regulator of opioid analgesia in vivo. Despite this apparent contradiction and the previously demonstrated physiological antagonism between these compounds in their traditional formats and conventionally used concentrations, my novel treatment process demonstrated a synergistic relationship period of time, and that an effective and efficacious opioid-induced analgesia results within the living subject from the process.

Unfortunately, because my prior invention requires the concurrent administration of two different self-contradicting and physiologically antagonistic compounds, SP and morphine, it presents difficulties in successfully establishing and testing the appropriate concurrent dosages for efficacious and safe administration in humans, as reflected by FDA and NIH clinical testing guidelines.

While morphine is the prototype opioid analgesic or painkiller, its complex alkaloid characteristics differ greatly from those of peptides, and SP is a peptide. In subsequent research, therefore, collaborators and I combined the active pharmacological domains of SP and the peptide endomorphin-2 into one chemical entity: a novel seven amino acid peptide chimera, designated ESP7. Repeated administration of the chimeric molecule into the rat spinal cord milieu produced analgesia mediated by the MOR without a loss of potency over a 5-day time course. Essentially, ESP7 represented a non-tolerance forming compound with future potential as a specialized spinal analgesic for control of acute and/or chronic pain. (Foran, et al., A Substance P-opioid chimeric peptide as a unique non-tolerance-forming analgesic, 97 Proceedings of the National Academy of Sciences 13 (2000))

Although ESP7 provided the advantage of a single analgesic molecule, it has several unfortunate disadvantages. Operationally, the peptide chemical nature of ESP7 restricts its effective dosage and time-effect relationship within the CNS due to significant metabolism in the blood stream. This is supported by collected pharmacological data indicating significant difficulties encountered by peptide drug candidates for crossing the mammalian blood-brain barrier (BBB) (Egleton R D, Abbruscato T J, Thomas S A, Davis T P Transport of opioid peptides into the central nervous system. J Pharm Sci 1998; 87(11):1433–9), as well as absorption after oral administration. (Borchardt R, Optimizing oral absorption of peptides using prodrug strategies. J Control Release 1999;62(1–2):231–8) Because of this, ESP7 envisioned intrathecal administration and administration through other means could yield short duration or no analgesia. Additionally, the peptide endomorphin-2 does not have the full analgesic effect of morphine.

Morphine is a relatively complex organic molecule, termed an alkaloid due to its positively charged nitrogen group, unlike the endogenous peptide endomorphin-2 which provided the analgesic moiety in ESP7. Morphine is a highly efficacious MOR-selective opioid analgesic and will cross the human BBB, as will its active metabolite morphine 6-glucuronide. (Stain-Texier F, Boschi G, Sandouk P, Scherrmann J M, Elevated concentration of morphine 6-beta-D-glucuronide in brain extracellular fluid despite low blood-brain barrier permeability. Br J Pharmacol 1999; 128(4):917–24)

Substance P, however, is a peptide. Chimeric hybrid molecules possessing an alkaloid moiety and a peptide moiety are unknown to the literature of analgesia and to clinical practice. Chimeric hybrid molecules possessing an alkaloid moiety to activate the human MOR and a peptide moiety to concurrently activate the human SP receptor (SPR) are unknown to the literature of analgesia and to clinical practice. Chimeric hybrid molecules comprised of one moiety with a chemically modified morphine molecule to activate the human MOR and another moiety with a SP fragment to activate the human SPR are unknown to the literature of analgesia and to clinical practice.

Another major challenge is to design a molecule that will cross the BBB and produce analgesia in a living subject, while inhibiting tolerance development and dependence formation. Such a molecule should be structured in such a way as to activate simultaneously the MOR and SPR domains in the PNS and/or CNS. With respect to both morphine and SP, a variety of alkaloid morphine and SP peptide fragments can be synthesized, having potentially different pharmacological effects if bound to another moiety. No obvious method is known for the SP moiety to be cross-linked to a morphine alkaloid moiety in a fashion that the resulting molecule will allow simultaneous activation of both the MOR and SPR receptors. Chimeric hybrid molecules with a moiety comprised of a chemically modified morphine molecule to provide the method to transport active SP fragments across the mammalian blood brain barrier are unknown to the literature of analgesia and to clinical practice.

Presently there also are no analgesic opioid molecules or chimeras that have been developed that achieve effective analgesia for mammalian acute or chronic pain without significant tolerance development and dependence formation.

Objects and Advantages. I have invented novel and useful compositions and methods employing heretofore unknown morphine-SP hybrid chimeras, as I have described below. Several objects and advantages of my present invention are:

a. a molecule that can be dosed to produce effective analgesia in a living subject, i.e., a mammal (an animal class which includes humans), while inhibiting tolerance development;
b. a molecule that can be dosed to produce effective analgesia in a living subject while inhibiting dependence formation;
c. a molecule that can be dosed to produce effective opioid analgesia and that can be administered through a variety of methods of clinical administration, including oral, systemic and intrathecal administration;
d. a molecule that can be dosed to produce effective opioid analgesia without significant restriction on its effective dosage and time-effect relationship within the CNS due to metabolism in the blood stream;
e. a molecule that can be dosed to yield effective opioid analgesia with a reduction in the likelihood of undesirable side effects;
f. a molecule that can be dosed to produce effective opioid analgesia with a reduction in the likely severity of undesirable side effects that become manifested by the patient;
g. an opioid analgesic that can be dosed for administration to children without undue tolerance development;
h. an opioid analgesic that can be dosed for administration to children without undue dependence formation; and
i. an opioid analgesic suitable for PCA in the treatment of chronic and/or acute pain.

Additional objects and advantages of my present invention are:

a. to provide a method for treating pain with opioid analgesia and little or no opioid tolerance development;
b. to provide a method for treating pain with opioid analgesia and little or no opioid dependence formation;
c. to provide a method for treating pain with opioid analgesia with reduced likelihood of undesirable side effects;
d. to provide a method of opioid analgesia for PCA for acute and/or chronic pain; and
e. to provide a method of treating drug abuse by administering as a substitute for the abused drug an analgesic that elicits little or no tolerance development or dependency formation and thereafter adjusting the dosage as tolerance and/or dependence is modulated.

Still further objects and advantages will become apparent from a consideration of the following description of my invention.

BRIEF SUMMARY OF THE INVENTION

The present invention provides composition of matter for and methods of treating pain using novel chimeric hybrid molecules containing an opioid moiety of chemically modified morphine that binds to and activates an MOR and a SP peptide fragment moiety that binds to and activates an SPR.

The present invention includes a family of chimeric hybrid molecules in which the alkaloid morphine or its active metabolite morphine 6-glucuronide are by design carriers of active SP peptide fragments across the mammalian BBB. I have designed this heretofore-unknown family of hybrid, chimeric molecules with unique molecular hinges. This novel family of chimeric hybrid compounds can provide opioid analgesia in living subjects while inhibiting tolerance development and dependence formation. These chimeric hybrid compounds can also be used for drug abuse treatment. The hybrid alkaloid/peptide analgesics may be administered systemically, intrathecally or more preferably, orally.

In one embodiment, the independent functional domains consisting of chemically modified morphine and a SP fragment are covalently cross linked through the four carbon organic molecule succinic acid. In another embodiment, the independent functional domains consisting of chemically modified morphine and a SP fragment are covalently cross linked through the four carbon organic molecule gamma-hydroxy butyric acid. In another embodiment, the independent functional domains consisting of chemically modified morphine and a SP fragment are covalently cross linked through the six carbon carbohydrate d-glucuronic acid. The use of three such molecules, succinic acid, gamma-hydroxy butyric acid, and d-glucuronic acid, as molecular hinges to cross link two active pharmacological domains of disparate chemical nature, i.e., a multi-ringed opioid alkaloid structure and a linear peptide structure, is not intuitively obvious or predictable from the prior art. The use of succinic acid, gamma-hydroxy butyric acid, and d-glucuronic acid, as molecular hinges to cross link a pharmacologically active peptide to a pharmacologically active opioid is novel and unknown to the literature of analgesia and to clinical practice.

The chimeric hybrid molecule may be designed to have a plurality of SP moieties consisting of pharmacologically active COOH-terminal fragments of SP and a plurality of opioid alkaloid moieties consisting of morphine chemically modified at its 6' hydroxyl group. The plurality of opioid moieties are each designed to bind to and activate an MOR. The plurality of SP fragments are each designed to bind to and activate the an. Because the MOR- and SPR-activating domains are of chemically different compositions, i.e., a multi-ringed alkaloid structure and a linear peptide structure, respectively, it is not intuitively obvious that they may be combined in a functionally active molecule. This is achieved, however, by incorporating a novel molecular hinge region consisting of succinic acid, or gamma-hydroxy butyric acid, or d-glucuronic acid. The existence of functionally active chimeric hybrid molecules, of internally differing chemical nature, combining MOR- and SPR-activating domains linked by a novel molecular hinge are unknown to the literature of analgesia and to clinical practice.

The invention provides pharmaceutical compositions including hybrid alkaloid chimeric molecules and a pharmaceutically acceptable carrier useful for the treatment of pain. It represents composition of matter for and methods of treating pain using novel hybrid alkaloid/peptide chimeric molecules containing an opioid and SP moiety designed to achieve coincident activation of populations of MORs and SPRs as a novel pain treatment without tolerance and dependence. The hybrid alkaloid/peptide analgesics may be administered systemically or more preferably, orally. Solubility, absorption, and penetration through the human BBB will be markedly enhanced due to the hydrophilic properties of morphine. The invention therefore provides novel method and composition of matter for and methods for treating pain using chemically modified morphine to serve both as an opioid analgesic as well as a pharmaceutically acceptable carrier for SP peptide absorption and stability after systemic administration as well as penetration through the human BBB. In these novel composition and design attributes, hybrid alkaloid chimeric molecules differ substantially from prior art including the peptide ESP7.

The design of novel hybrid alkaloid chimeric molecules encompassing three chemically disparate functional domains, i.e., a ringed alkaloid MOR-activation domain, a peptide SPR-activation domain, and a flexible organic acid hinge domain, is unknown to the preclinical and clinical literature of pain and analgesia.

A desired objective of the present invention is that the hybrid alkaloid/peptide chimeric molecules can be administered to produce clinically efficacious opioid analgesia with little or no development of opioid tolerance. With little or no tolerance development, escalating dosages will not be required to achieve the same pain killing effect and opioid dependence formation and undesirable side effects associated with escalating opioid dosages will be avoided or markedly reduced.

Detailed descriptions of one or more embodiments of the invention are described below. The novelty of the invention, as amply described above, will be apparent from the detailed description of structure and synthesis and from the claims. In the specification and the appended claims, the singular forms include plural referents unless the context clearly dictates otherwise. All technical and scientific terms used herein have the same meaning as commonly understood by one of ordinary skill in the art to which this invention belongs. Unless expressly stated otherwise, the techniques employed or contemplated herein are standard methodologies well known to one of ordinary skill in the art. The examples of embodiments are for illustration purposes only. All patents and publications cited in this specification are incorporated herein by reference.

DETAILED DESCRIPTION OF THE INVENTION

Figure 1:
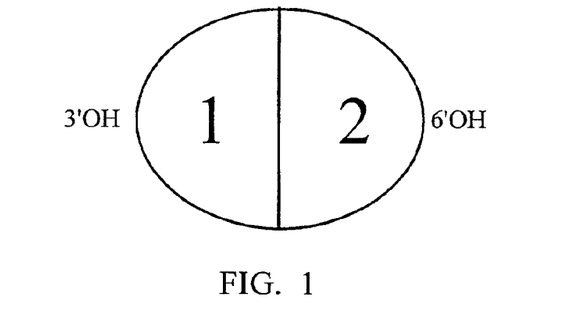
FIG. 1 illustrates two domains of the morphine nucleus, one being a conjugation domain useable to synthesize the chimeric hybrid compounds and the other being the active domain that activates the MOR.
Figure 2:
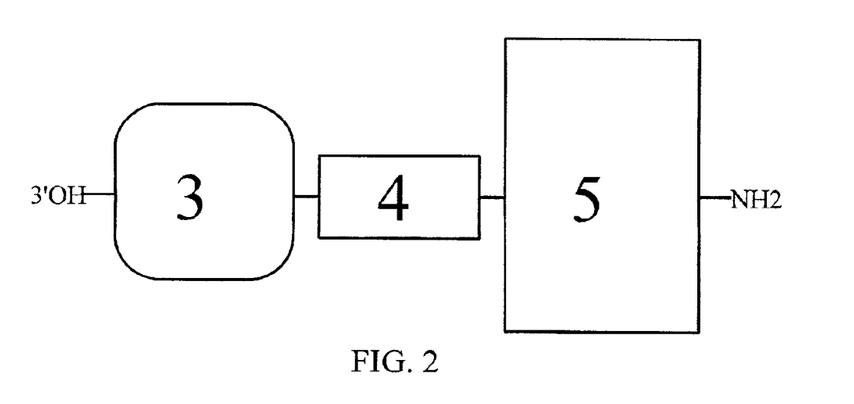
FIG. 2 illustrates schematically how a chimeric hybrid molecule is constructed of three, linked components, i.e., a morphine nucleus, a linker-hinge and an SP fragment.

Description—FIGS. 1 and 2

The present invention provides hybrid alkaloid chimeric molecules having an MOR binding and activation moiety and an SPR binding and activation moiety. The hybrid alkaloid chimeric molecules are designed to bind to and activate populations of MORs and SPRs located primarily within the human CNS, but also in the human PNS, involved in pain mediation and analgesic responses. While the alkaloid morphine and the peptide SP frequently exhibit slight cross reactivity to other opioid and tachykinin receptor types, respectively, they are generally characterized, as exhaustively detailed in the literature, by a very high degree of affinity for the MOR and SPR, respectively. The preservation of independent binding and activation moieties in one hybrid alkaloid/peptide molecule containing a multi-ringed alkaloid structure and a linear peptide structure, is not described in the prior art and distinguishes the present invention as novel and not evolving from prior invention.

The existence of functionally active chimeric hybrid molecules, of internally differing chemical nature, combining MOR- and SPR-activating domains linked by a novel molecular hinge are unknown to the literature of analgesia and to clinical practice. Because the MOR- and SPR-activating domains are of chemically different compositions, i.e., a multi-ringed alkaloid structure and a linear peptide structure, respectively, it is not intuitively obvious that they may be combined in a functionally active molecule.

I have achieved this by design and incorporation of a novel chemical linker-hinge region consisting of succinic acid, or gamma-hydroxy butyric acid, or d-glucuronic acid, to connect within a single molecule an alkaloid MOR-activation domain and a peptide SPR-activation domain that are modified to be compatible with that hinge. The design of novel hybrid alkaloid chimeric molecules encompassing three chemically disparate functional domains, i.e., a ringed alkaloid MOR-activation domain, a peptide SPR-activation domain, and a flexible organic acid hinge domain, is unknown to the preclinical and clinical literature of pain and analgesia.

The chimeric multi-ringed alkaloid structure of morphine linked to the linear peptide structure of SP is illustrated in FIG. 1 and FIG. 2. FIG. 1 illustrates that a morphine nucleus can be considered as divided into two domains, one of which is a conjugation domain 2 useable to synthesize the chimeric hybrid compounds from the 6'OH position on the morphine nucleus and the other of which is an active domain 1 that activates the MOR. FIG. 2 illustrates schematically how a chimeric hybrid molecule is constructed of three interlocking components, the alkaloid morphine nucleus 3, a chemical-linker hinge 4, and a peptide SP fragment 5. The chemical linker-hinge 4 links to the alkaloid morphine nucleus 3 at its 6'OH position. The chemical linker-hinge 4 also links to the peptide SP fragment 5. The linker-hinge allows the N-terminal opioid receptor binding moiety or active domain of the morphine nucleus fragment of the hybrid chimeric molecule be able to activate an MOR and the C-terminal SP receptor agonist binding moiety of the SP fragment to be able to activate an SPR.

The chimeric hybrid molecule may be designed to have a plurality of SP moieties consisting of pharmacologically active COOH-terminal fragments of SP and a plurality of opioid alkaloid moieties consisting of morphine chemically modified at its 6'hydroxyl group. The plurality of opioid moieties are each designed to bind to and activate an MOR. The plurality of SP fragments are each designed to bind to and activate an SPR.

I refer to the following amino acid sequences using the Seq. Id. Nos. below:

| SEQ. ID. NO. | SEQUENCE |
|---|---|
| 1 | Lys Pro Gln Gln Phe Phe Gly Leu Met |
| 2 | Gln Gln Phe Phe Gly Leu Met |
| 3 | Phe Phe Gly Leu Met |

Nine preferred embodiments of the present invention are listed in table 1

TABLE 1

| Embodiment # | μ receptor agonist | Hinge | SP receptor agonist | Sequence |
|---|---|---|---|---|
| 1 | Morphine | D-Glucuronic Acid | N-Acetylsubstance P (3–11): Ac-KPQQFFGLM-NH2 | SEQ ID. NO. 1 |
| 2 | Morphine | D-Glucuronic Acid | Substance P (5–11): QQFFGLM-NH2 | SEQ. ID. NO. 2 |
| 3 | Morphine | D-Glucuronic Acid | Substance P (7–11): FFGLM-NH2 | SEQ. ID. NO. 3 |
| 4 | Morphine | Succinic acid | N-Acetylsubstance P (3–11): Ac-KPQQFFGLM-NH2 | SEQ. ID. NO. 1 |
| 5 | Morphine | Succinic acid | Substance P (5–11) QQFFGLM-NH2 | SEQ. ID. NO. 2 |
| 6 | Morphine | Succinic acid | Substance P (7–11): FFGLM-NH2 | SEQ. ID. NO. 3 |
| 7 | Morphine | Gamma —OH Butyric Acid | N-Acetylsubstance P (3–11): Ac-KPQQFFGLM-NH2 | SEQ. ID. NO. 1 |
| 8 | Morphine | Gamma —OH Butyric Acid | Substance P (5–11) QQFFGLM-NH2 | SEQ. ID. NO. 2 |
| 9 | Morphine | Gamma —OH Butyric Acid | Substance P (7–11): FFGLM-NH2 | SEQ ID. NO. 3 |

Advantages of the Present Invention

The advantages of morphine as an analgesic that can cross the BBB are well known to the literature. The advantages of simultaneous activation of an MOR and SPR to modulate the activation of the MOR and to reduce or eliminate tolerance development and dependence formation are also known from the literature, such as a prior invention of mine (U.S. Pat. No. 5,891,842) and the work of colleagues of mine and I identified above relating to ESP7.

From the description above, a number of advantages of my chimeric hybrid analgesic molecules become evident:

a. the molecule will inhibit tolerance development while being dosed to provide morphine opioid analgesia;
b. the molecule will inhibit dependence formation while being dosed to provide morphine opioid analgesia;
c. the molecule can be administered through a variety of methods of clinical administration, in addition to intrathecal administration;
d. the molecule will not have the significant dosage and time-effect restrictions of peptides due to metabolism in the blood stream;
e. because of the modulation of an MOR by SPR activation, an escalating dosage typical of morphine is not required;
f. because the escalating dosage typical of morphine is not required, the likelihood and severity of undesirable effects associated with escalating morphine dosage will be reduced; and
f. the molecule can be administered as a substitute for an abused opioid drug and, because the molecule elicits little or no tolerance development or dependency formation, its dosage can thereafter be adjusted as tolerance and/or dependence is modulated.

Further advantages will become apparent to those skilled in the art.

Making My Invention. The present invention can be made by a person skilled in the art, as follows. The separate MOR- and SPR-activating moieties are synthesized and purified or isolated from natural sources and then chemically cross-linked to form hybrid alkaloid/peptides chimeric molecules. All syntheses utilize well-established standard organic chemistry techniques and reagents. SP peptide fragment moieties are synthesized prior to covalent attachment to the morphine nucleus (FIG. 1). For these purposes, a variety of peptide synthesis methods are common in the art, including synthesis using an automated peptide synthesizer and employing Fmoc amino acids. (Merrifield, Science 232: 241–247 (1986); Barany, et al, Intl. J Peptide Protein Res. 30: 705–739 (1987); Kent, Ann. Rev. Biochem. 57:957–989 (1988), and Kaiser, et al, Science 243: 187–198 (1989)) SP peptide fragments are purified to over 99% chemical purity using standard peptide purification techniques such as reverse-phase high-pressure liquid chromatography (HPLC). The chemical structures of SP peptide fragments, purified by HPLC, are confirmed by mass spectroscopic analysis.

Morphine is chemically modified by covalent attachment at its 6'OH group to the hinge-forming organic molecules described above: d-glucuronic acid, succinic acid, gamma-hydroxy butyric acid. Chemically modified morphine derivatives, i.e., morphine-6-glucuronide, morphine-6-hemi-succinate, morphine-6-gamma-hydroxy butyrate, are covalently attached to SP peptide fragments using standard condensing agents such as water soluble carbodiimide (CDI).

Alternatively, SP peptide fragments are chemically modified by covalent attachment at their free amino groups to the hinge-forming organic molecules described above: d-glucuronic acid, succinic acid, gamma-hydroxy butyric acid. Chemically modified SP peptide fragments, i.e., SP fragment-glucuronide, SP fragment-hemi-succinate, SP fragment-gamma-hydroxy butyrate, are covalently attached to morphine using standard condensing agents such as water soluble CDI.

Prior to pharmacological testing, the novel chimeric hybrid alkaloid/peptide molecules comprising a cyclic alkaloid MOR-activating moiety and an SPR-activating peptide moiety (such as those in Table 1) are purified to over 99% purity by standard chromatographic techniques such as reverse-phase HPLC. This represents less than about 1% chemical precursors or non-peptide chemicals in the final preparations. The chemical structures of chimeric hybrid alkaloid/peptide molecules are confirmed by mass spectroscopic analysis. The chimeric hybrid molecules are then subjected to standard pharmacological testing.

Preclinically, a well-established method is used to assess the analgesic properties of the novel chimeric hybrid compounds, that being the tail flick test, which is administered to rats following parenteral or CNS administration. Additional tests of analgesic responsiveness include the paw withdrawal and hotplate tests, i.e., methods well-established as common in the art. Preclinical testing of analgesia and tolerance development is conducted by administration of the chimeric hybrid compounds over time and alternatively using opioid and SP blockers in well-established analgesic testing methods. Further preclinical and clinical testing is conducted in conformity with governmental drug regulations.

Using My Invention

The present invention further provides methods of treating a mammal for relief of pain by administering a pharmaceutical composition (as described above) in order to produce analgesia in the subject/patient. The invention is used by persons skilled in the art, as follows: Pharmaceutical compositions of the invention are formulated to be compatible with their intended routes of administration, e.g., parenteral, intradermal, subcutaneous, injectable, intravenous, oral, intradermal, subcutaneous, transdermal (topical), transmucosal, and rectal administration.

Solutions or suspensions suitable for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates. The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, sterile or bacteriostatic water, or phosphate buffered saline (PBS). In all cases, the compositions must be sterile and should be fluid to the extent that they are easily injectable by syringe. Proper fluidity may be maintained by the use of a coating such as lecithin, by the maintenance of the required particle size in the case of dispersion and by the use of surfactants. Preservation of chemical and pharmaceutical integrity is achieved by various antibacterial and antifungal agents: e.g., parabens, chlorobutanol, phenol, ascorbic acid, thimerosal, etc. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., chimeric hybrid molecules) in the required dosage in an appropriate solvent with one or a combination of ingredients enumerated above, as required, followed by filtered sterilization.

Oral compositions generally include an inert diluent or an edible carrier. They can be enclosed in gelatin capsules or compressed into tablets. For the purpose of oral therapeutic administration, the active compound can be incorporated with binders and used in the form of tablets, troches, or capsules. Pharmaceutical binding agents, and/or adjuvant material can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide.

Suitable intradermal, subcutaneous, transdermal (topical), and transmucosal formulations include: gels, creams, solutions, emulsions, suspensions, carbohydrate polymers, biodegradable matrices thereof, vapors, mists, aerosols and other inhalants, and skin patches. Rectal formulations also include suppositories and enemas.

Examples of suitable pharmaceutical carriers for the various forms of administration include any of the standard pharmaceutically accepted carriers known to those of ordinary skill in the art. Examples of pharmaceutical carriers include but are not limited to buffered saline solution, water, emulsions, various wetting agents, tablets, coated tablets and capsules. Besides an effective amount of the compounds described in the present invention, pharmaceutical compositions may include suitable diluents, preservatives, solubilizers, emulsifiers, adjuvant and/or carriers. Examples of optional ingredients which may be included in the pharmaceutical compositions of the present invention include antioxidants; low molecular weight polypeptides; proteins such as serum albumin, gelatin or immunoglobulins; amino acids such as glycine; chelating agents; sugar alcohols.

Because of the modulation of opioid tolerance and dependence, the invention may also be used for drug abuse intervention through administration of one or more embodiments of the chimeric hybrid analgesics which are the subjects of the invention in substitution for the drug to which the patient became tolerant and/or on which the patient became dependent.

Conclusions, Ramifications and Scope. The reader thus will see that my invention provides novel and useful composition of matter for and methods of treating pain and drug abuse using novel chimeric hybrid molecules containing an opioid moiety of chemically modified morphine that binds to and activates the MOR and a SP peptide fragment moiety that binds to and activates the SPR, to produce opioid analgesia in a living subject with little or no tolerance development and dependence formation.

While my description contains many specifications, these should not be construed as limitations on the scope of my invention, but rather as an exemplification of one or more of the preferred embodiments of my invention. Other variations are possible. Accordingly, the scope of my invention should be determined by the appended claims and their legal equivalents and not by the embodiments illustrated in the foregoing description.

I claim:

1. A conjugate molecule comprising a mammalian mu (μ) opioid receptor agonist covalently linked to a mammalian substance P receptor agonist, wherein one agonist is a peptide and one is a non-peptide.

2. A conjugate molecule of claim 1 wherein the molecule induces analgesia when administered in a mammal.

3. A conjugate molecule of claim 2 wherein analgesia is produced in the mammal with tolerance development markedly less than that of morphine.

4. A conjugate molecule comprising a modified morphine as the mu opioid receptor agonist covalently attached to D-glucuronic acid, the cross-linker, via an o-glycosidic linkage between the 6-OH of modified morphine and the 1-OH group of the D-glucuronic acid and a Substance P fragment of SEQ ID NO:1 also covalently attached to the D-glucuronic acid via a peptide bond between the COOH group of the D-glucuronic acid and the epsilon-amino group of Substance P fragment [N-acetyl SP(3–11)].

5. The conjugate molecule of claim 4 wherein the molecule induces analgesia when administered in a mammal.

6. The conjugate molecule of claim 5 wherein analgesia is produced in the mammal with tolerance development markedly less than that of morphine.

7. A conjugate molecule comprising a modified morphine as the mu opioid receptor agonist covalently attached to the dicarboxylic succinic acid, the cross-linker, via an ester linkage between the 6-OH of modified morphine and the COOH group of the dicarboxylic succinic acid, and a Substance F fragment of SEQ ID NO:1 also covalently attached to the dicarboxylic succinic acid via a peptide bond between the COOH group of the dicarboxylic succinic acid and the epsilon-amino group of Substance P fragment [N-acetyl SP(3–11)].

8. The conjugate molecule of claim 7 wherein the molecule induces analgesia when administered in a mammal.

9. The conjugate molecule of claim 8 wherein analgesia is produced in the mammal with tolerance development markedly less than that of morphine.

10. A conjugate molecule comprising a modified morphine as the mu opioid receptor agonist covalently attached to gamma-hydroxy butyric acid, the cross-linker, via an ether linkage between the 6-OH of modified morphine and the 4-OH group of gamma-hydroxy butyric acid, and a Substance P fragment of SEQ ID NO:1 also covalently attached to gamma-hydroxy butyric acid via a peptide bond between the COOH group of gamma-hydroxy butyric acid and the epsilon-amino group of Substance P fragment [N-acetyl SP(3–11)].

11. The conjugate molecule of claim 10 wherein the molecule induces analgesia when administered in a mammal.

12. The conjugate molecule of claim 11 wherein analgesia is produced in the mammal with tolerance development markedly less than that of morphine.

13. A conjugate molecule comprising a modified morphine as the mu opioid receptor agonist covalently attached to D-glucuronic acid, the cross-linker, via an o-glycosidic linkage between the 6-OH of modified morphine and the 1-OH group of the D-glucuronic acid and a Substance P fragment of SEQ ID NO:2 also covalently attached to the D-glucuronic acid via a peptide bond between the COOH group of the D-glucuronic acid and the alpha-amino group of Substance P fragment [SP(5–11)].

14. The conjugate molecule of claim 13 wherein the molecule induces analgesia when administered in a manual.

15. The conjugate molecule of claim 14 wherein analgesia is produced in the mammal with tolerance development markedly less than that of morphine.

16. A conjugate molecule comprising a modified morphine as the mu opioid receptor agonist covalently attached to the dicarboxylic succinic acid, the cross-linker, via an ester linkage between the 6-OH of modified morphine and the COOH group of the dicarboxylic succinic acid, and a Substance P fragment of SEQ ID No:2 also covalently attached to the dicarboxylic succinic acid via a peptide bond between the COOH group of the dicarboxylic succinic acid and the alpha-amino group of Substance P fragment [SP(5–11)].

17. The conjugate molecule of claim 16 wherein the molecule induces analgesia when administered in a mammal.

18. The conjugate molecule of claim 17 wherein analgesia is produced in the mammal with tolerance development markedly less than that of morphine.

19. A conjugate molecule comprising a modified morphine as the mu opioid receptor agonist covalently attached to gamma-hydroxy butyric acid, the cross-linker, via an ether linkage between the 6-OH of modified morphine and the 4-OH group of gamma-hydroxy butyric acid, and a Substance P fragment of SEQ ID NO:2 also covalently attached to gamma-hydroxy butyric acid via a peptide bond between the COOH group of gamma-hydroxy butyric acid and the alpha-amino group of Substance P fragment [SP(5–11)].

20. The conjugate molecule of claim 19 wherein the molecule induces analgesia when administered in a mammal.

21. The conjugate molecule of claim 20 wherein analgesia is produced in the mammal with tolerance development markedly less than that of morphine.

22. A conjugate molecule comprising a modified morphine as the mu opioid receptor agonist covalently attached to D-glucuronic acid, the cross-linker, via an o-glycosidic linkage between the 6-OH of modified morphine and the 1-OH group of the D-glucuronic acid and a Substance P fragment of SEQ ID NO:3 also covalently attached to the D-glucuronic acid via a peptide bond between the COOH group of the D-glucuronic acid and the alpha-amino group of Substance P fragment [SP(7–11)].

23. The conjugate molecule of claim 22 wherein the molecule induces analgesia when administered in a mammal.

24. The conjugate molecule of claim 23 wherein analgesia is produced in the mammal with tolerance development markedly less than that of morphine.

25. A conjugate molecule comprising a modified morphine as the mu opioid receptor agonist covalently attached to the dicarboxylic succinic acid, the cross-linker, via an ester linkage between the 6-OH of modified morphine and the COOH group of the dicarboxylic succinic acid, and a Substance P fragment of SEQ ID NO:3 also covalently attached to the dicarboxylic succinic acid via a peptide bond between the COOH group of the dicarboxylic succinic acid and the alpha-amino group of Substance P fragment [SP(7–11)].

26. The conjugate molecule of claim 25 wherein the molecule induces analgesia when administered in a mammal.

27. The conjugate molecule of claim 26 wherein analgesia is produced in the mammal with tolerance development markedly less than that of morphine.

28. A conjugate molecule comprising a modified morphine as the mu opioid receptor agonist covalently attached to gamma-hydroxy butyric acid, the cross-linker, via an ether linkage between the 6-OH of modified morphine and the 4-OH group of gamma-hydroxy butyric acid, and a Substance P fragment of SEQ ID NO:3 also covalently attached to gamma-hydroxy butyric acid via a peptide bond between the COOH group of gamma-hydroxy butyric acid and the alpha-amino group of Substance P fragment [SP(7–11)].

29. The conjugate molecule of claim 28 wherein the molecule induces analgesia when administered in a mammal.

30. The conjugate molecule of claim 29 wherein analgesia is produced in the mammal with tolerance development markedly less than that of morphine.

31. A pharmaceutical composition of claims 1, 4, 7, 10, 13, 16, 19, 22, 25, or 28 and a pharmaceutically acceptable diluent.

32. A pharmaceutical composition of claims 1, 4, 7, 10, 13, 16, 19, 22, 25, or 28 comprising an adjuvant.

33. A method for producing analgesia in a mammal, by administering to said mammal, a conjugate molecule of any one of claims 1, 2, 5, 8, 11, 14, 17, 20, 23, 26 and 29.

34. A method of claim 33 wherein the mammal is a human.

35. A method for producing a conjugate molecule comprising a mammalian mu ($\mu$) opioid receptor agonist covalently linked to a mammalian substance P receptor agonist, wherein the mu ($\mu$) opioid receptor agonist is a non-peptide and the substance P receptor agonist is a peptide, comprising:

a. the selection of a non-peptide mu opiold receptor agonist, a cross-linker and a peptide substance P receptor agonist such that when the mu opioid receptor agonist is modified and covalently linked to the cross-linker and the cross-linker is covalently linked via a peptide bond to the substance P receptor agonist, the cross-linker will be able to flex such that the mu opioid receptor agonist and the substance P receptor agonist contemporaneously activate their respective receptors, and b. the modification of the mu opioid receptor agonist such that it can be covalently attached to a flexible hinge cross-linker, the covalent attachment of the modified mu opioid receptor agonist to the flexible hinge cross-linker, and the covalent attachment of the cross-linker via a peptide bond to the Substance P fragment.

36. A method for producing a conjugate molecule comprising a mammalian mu ($\mu$) opioid receptor agonist covalently linked to a mammalian substance P receptor agonist, wherein the mu ($\mu$) opioid receptor agonist is a peptide and the substance P receptor agonist is a non-peptide, comprising:

a. the selection of a peptide mu opioid receptor agonist, a cross-linker and a non-peptide substance P receptor agonist such that when the mu opioid receptor agonist is modified and covalently linked via a peptide bond to the cross-linker and the cross-linker is covalently linked to the substance P receptor agonist, the cross-linker will be able to flex such that the mu opioid receptor agonist and the substance P receptor agonist contemporaneously activate their respective receptors, and b. the modification of the mu opioid receptor agonist such that it can be covalently attached to a flexible hinge cross-linker via a peptide bond, the covalent attachment of the modified mu opioid receptor agonist to the flexible hinge cross-linker via a peptide bond, and the covalent attachment of the cross-linker to the substance P fragment.

* * * * *

SEQUENCE LISTING

<160> NUMBER OF SEQ ID NOS: 3

<210> SEQ ID NO 1
<211> LENGTH: 9
<212> TYPE: PRT
<213> ORGANISM: mammalian

<400> SEQUENCE: 1

Lys Pro Gln Gln Phe Phe Gly Leu Met

-continued

```
1               5

<210> SEQ ID NO 2
<211> LENGTH: 7
<212> TYPE: PRT
<213> ORGANISM: mammalian

<400> SEQUENCE: 2

Gln Gln Phe Phe Gly Leu Met
1               5

<210> SEQ ID NO 3
<211> LENGTH: 5
<212> TYPE: PRT
<213> ORGANISM: mammalian

<400> SEQUENCE: 3

Phe Phe Gly Leu Met
1               5
```